United States Patent

Häberle et al.

Patent Number: 5,210,247
Date of Patent: May 11, 1993

[54] ORGANOSILYLALKYLAROMATIC COMPOUNDS

[75] Inventors: Norman Häberle, Munich; Wolfgang Haas, Germering; Leonhard Brader, Fischbachau; Franz-Heinrich Kreuzer, Martinsried, all of Fed. Rep. of Germany

[73] Assignee: Consortium für elektrochemische Industrie GmbH, Munich, Fed. Rep. of Germany

[21] Appl. No.: 600,659

[22] Filed: Oct. 22, 1990

[30] Foreign Application Priority Data

Oct. 26, 1989 [DE] Fed. Rep. of Germany ........ 3935638

[51] Int. Cl.$^5$ ............................. C07F 7/04; C07F 7/08
[52] U.S. Cl. .................................... 556/413; 556/415; 556/436; 556/437; 556/438; 556/425; 556/443
[58] Field of Search ............... 556/415, 436, 437, 438, 556/413, 425, 443

[56] References Cited

U.S. PATENT DOCUMENTS 4,914,221  4/1990  Winkler et al. ................. 556/436

FOREIGN PATENT DOCUMENTS

| 0163495 | 5/1985 | European Pat. Off. |
| 0291082 | 5/1987 | European Pat. Off. |
| 0282294 | 3/1988 | European Pat. Off. |
| 0322703 | 12/1988 | European Pat. Off. |
| 0385732 | 5/1990 | European Pat. Off. |
| 0304720 | 9/1988 | Fed. Rep. of Germany ...... 556/436 |
| 2245663 | of 1973 | France. |

OTHER PUBLICATIONS

J. Chem. Soc. (1964) pp. 1548-1553 Bott et al.
CA-(vol. 55) 21039g (1961) Chernyshev et al.

Primary Examiner—José Dees
Assistant Examiner—Joseph M. Conrad

[57] ABSTRACT

The present invention relates to compounds of the formula

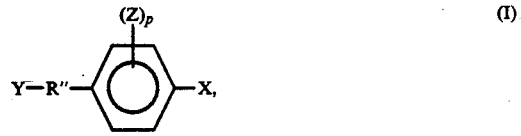

in which
Y represents an organosilicon radical;
R" represents a divalent radical which connects the radical Y to the benzene ring via a chain of at least three atoms;
X represents a radical of the formula —COOH, —CN, —CHO, —NH$_2$ or —OH, in which it is possible to block the hydroxyl group with a protecting group;
Z represents the same or different substituents in the 2-, 3-, 5- or 6-position to the radical X, preferably hydrogen or halogen atoms; and
p represents a value of 0 to 4;

and the use of these and related compounds in the preparation of compounds having liquid-crystalline properties.

25 Claims, No Drawings

ORGANOSILYLALKYLAROMATIC COMPOUNDS

The present invention relates to organosilicon compounds containing a substituted benzene ring bonded directly or indirectly via an alkyl chain.

PRIOR ART

E. A. Chernyshev and N. G. Tolstika (Chemical Abstracts, Vol. 55, 21 039g, 1961) describe the preparation of 4-[trialkylsilyl($C_1$- to $C_2$)-alkyl]benzoic acids from the corresponding bromophenyl compounds by reaction with magnesium and $CO_2$. R. W. Bott et al (Journal of the Chemical Society, 1964, pages 1548-1553) discloses 4-[trimethylsilyl ($C_1$- to $C_4$)-alkyl]-chlorobenzenes. In the abovementioned literature references, the use of these compounds as starting materials for liquid crystals is not disclosed. EP-A-304,720 (laid open on 1 Mar. 1989, F. H. Kreuzer et al, Consortium für elektrochemische Industrie GmbH) describes the preparation of 4-dimethylsilylbenzoic acid from 1,4-dihalobenzene. The use of difunctional silanes in the preparation of liquid crystal displays is mentioned therein in general terms; however, the compounds presented therein are not suitable as starting materials for liquid crystals because of the steric hindrance of the dimethylsilyl group attached directly to the benzene ring.

It is, therefore, an object of the present invention to provide novel starting materials for the preparation of liquid crystals. Another object of the present invention is to provide novel silylated benzene derivatives as starting materials for liquid crystals. A further object of the present invention is to provide silylated benzene derivatives as starting materials for liquid crystals, in which the silyl group(s) in the liquid crystal prepared therefrom does not hinder its orientation because of its steric hindrance.

SUMMARY OF THE INVENTION

The foregoing objects and others which will become apparent from the following description are accomplished in accordance with this invention, generally speaking, by providing compounds of the formula

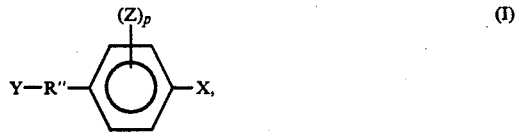

in which Y represents an organosilicon radical, R" represents a divalent radical which connects the Y radical to the benzene ring via a chain having at least three atoms, X represents a radical of the formula —COOH, —CN, —CHO, —$NH_2$ or —OH, in which it is possible for the hydroxyl group to be blocked by a protecting group, Z represents the same or different substituents in the 2-, 3-, 5- or 6-position to the radical X, preferably hydrogen or halogen atoms, and p has a value of from 0 to 4.

The radical R" in the above formula is preferably a radical or a substituted radical of the formula

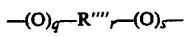

which q and s each represent, independently of each other, the number 0 or 1, and r has a value of from 1 to 3, and R"" is a divalent hydrocarbon radical having up to 20 carbon atoms and a divalent substituted hydrocarbon radical having up to 20 carbon atoms, and in particular, an alkylene, cycloalkylene, cycloalkenylene, arylene, alkarylene or aralkylene radical, with the proviso that q, r, s and R"" are selected so that the radical R" is a divalent radical which connects the radical Y to the benzene ring via a chain of at least three atoms.

The preferred substituents on the radical R"" are halogen atoms. However, R" and R"" are preferably unsubstituted.

DESCRIPTION OF THE INVENTION

The compounds of formula (I) of this invention are preferably those of formula (II)

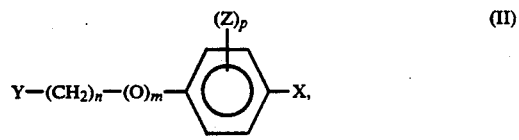

in which n represents an integer having a value of at least 2, m represents an integer having a value of 0 or 1, where the sum n+m is at least 3, and X, Y, Z and p are the same as above and n preferably has a maximum value of 20. In formulas (I) and (II), p preferably has the value 0. The radical Y in formulas (I) and (II) is preferably a linear silanyl or siloxanyl radical of formula (III)

or a cyclosiloxanyl radical of formula (IV)

where in the above formulas (III) and (IV), R represents the same or different hydrocarbon radicals having from 1 to 18 carbon atoms and substituted hydrocarbon radicals having from 1 to 18 carbon atoms, whose substituents are preferably halogen atoms, cyano radicals, mercapto groups or amino groups, t represents an integer having a value of at least 0, u represents an integer having a value of at least 2, and preferably not more than 8, v represents an integer having a value of at least 0, and preferably not more than 5, and more preferably not more than 1, and T represents a radical of the formula —R""—$SiR_2$—, where R and R"" are the same as above; t and u each preferably have a maximum value of 20, and in particular not more than 10, and more particularly not more than 5.

In particular, t has the value 1 or 2, and u has the value 2, 3 or 4.

Specific examples of radicals represented by R are fluoroalkyl radicals having from 1 to 18 carbon atoms.

The compounds described above can be advantageously prepared by the following processes:

Process (1)

Compounds of formula (II) are preferably prepared by (A) reacting compounds of the formula (V)

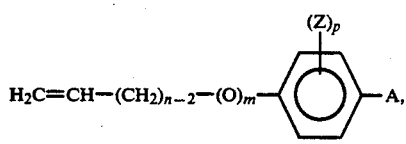

in which
- A is the same as Q or is a hydroxyl or carboxyl group which is protected by a protecting group, where
- Q is a halogen atom, preferably a chlorine or bromine atom, and n, m, p and Z are the same as above, with compounds of the formula Y—H in the presence of platinum metals and/or compounds thereof to give compounds of the formula

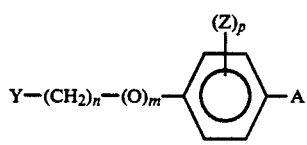

and (B1) if X in the desired product of formula (II) is to be a radical of the formula —COOH, then compounds of formula (VI), in which A is a radical with the meaning Q, are reacted with magnesium and subsequently with $CO_2$, or if compounds of formula (VI), in which A is a carboxyl radical, which is blocked by a protecting group, then the protecting group is removed, (B2) if X in the desired product of formula (II) is to be a radical of the formula —CN, then compounds of the formula (VI), in which A is a radical with the meaning Q, are reacted with cyanides, preferably with copper cyanide, (B3) if X in the desired product of formula (II) is to be a radical of the formula —OH and the radical A in the formula (VI) is a hydroxyl group which is blocked by a protecting group, then the protecting group is removed in a manner known per se, (B4) if X in the desired product of formula (II) is to be a radical of the formula —CHO, then compounds of formula (VI), in which A is a radical with the meaning Q, are reacted with magnesium and then with N,N-dimethylformamide and thereafter the product is subjected to acid hydrolysis in a manner known per se.

The hydrogen atom labelled by the "H" in the above-mentioned formula Y—H is preferably a hydrogen atom bonded directly to a silicon atom.

The preferred protecting group for a carboxyl group is a trialkylsilyl group, and in particular the trimethylsilyl group.

All catalysts which have been employed or could have been employed heretofore for the addition of hydrogen atoms bonded directly to Si atoms to aliphatically unsaturated compounds can be employed here. Examples of such catalysts are metallic and finely divided platinum, which may be supported on carriers, such as silicon dioxide, aluminum oxide or activated charcoal, compounds or complexes of platinum, such as platinum halides, for example $PtCl_4$, $H_2PtCl_6.6H_2O$, $Na_2PtCl_4.4H_2O$, platinum-olefin complexes, platinum-alcohol complexes, platinum-alcoholate complexes, platinum-ether complexes, platinum-aldehyde complexes, platinum-ketone complexes, including products of the reaction of $H_2PtCl_6.6H_2O$ and cyclohexanone, platinum-vinylsiloxane complexes, in particular platinum-divinyltetramethyldisiloxane complexes which contain or are free of detectable inorganically bound halogen, bis(gamma-picoline)-platinum dichloride, trimethylenedipyridineplatinum dichloride, dicyclopentadieneplatinum dichloride, (dimethyl sulfoxide)ethyleneplatinum(II) dichloride and products of the reaction of platinum tetrachloride with olefins and primary amines or secondary amines or primary and secondary amines, such as the product of the reaction of platinum tetrachloride dissolved in 1-octene with sec-butylamine, or ammoniumplatinum complexes as in EP-B 110,370.

The platinum catalyst is preferably employed in amounts of from 0.5 to 500 ppm by weight (parts by weight per million parts by weight), and more preferably from 2 to 400 ppm by weight, based on the elemental platinum and based on the total weight of the starting materials.

The reaction of the compound of formula (VI) as per step (B1) with magnesium to form the Grignard compound and the subsequent reaction of the Grignard compound with $CO_2$ are carried out in a manner known per se.

The reaction as per step (B2) is preferably carried out in the presence of CuCN at temperatures of from 80° C. to 250° C., preferably in an inert solvent.

The protecting groups present in formula (I) or removed in step (B3) are known per se. These are, in particular, the following groups: Trialkylsilyl groups, such as trimethylsilyl, tert-butyldimethylsilyl and triethylsilyl groups; alkoxymethylene groups, such as methoxymethylene and ethoxymethylene groups; and substituted or unsubstituted benzyl groups.

Preferred protecting groups are trialkylsilyl groups, alkyloxymethylene groups and ester groups, and more preferably the trimethylsilyl and methoxymethylene groups.

These groups can easily be removed under acidic or alkaline conditions, preferably at an elevated temperature.

If X in formula (I) or (II) is to be a hydroxyl group which is blocked by a protecting group, the abovementioned step (B3) is naturally superfluous.

Process (2)

Starting compounds of formula (V) in which m represents 0, i.e., those of formula (X)

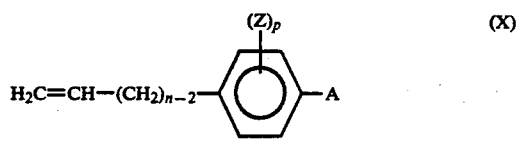

in which A, Z, n and p are the same as above, are preferably prepared by:

(A) reacting compounds of formula (VII)

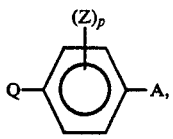 (VII)

in which
Q represents a halogen atom, preferably a chlorine or bromine atom, and
A is the same as Q or represents a hydroxyl group which is protected by a protecting group, and Z and p are the same as above, with magnesium to form Grignard compounds (VIII)

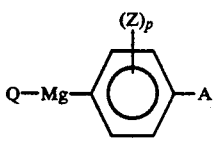 (VIII)

and then
(B) reacting the Grignard compounds of formula (VIII) with compounds of formula (IX)

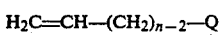
$H_2C=CH-(CH_2)_{n-2}-Q$ (IX)

to form compounds of formula (X)

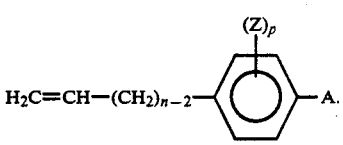 (X)

The reaction of compound (VIII) with compound (IX) is preferably carried out in the presence of lithium tetrachlorocuprate. Analogous reactions are described by S. B. Mirviss (Journal of Organic Chemistry, Volume 54, pages 1948-1951 (1989). In the present process, however, alkyl-aryl linkages are also possible at temperatures higher than 50° C. (which is not described in the above-cited literature reference), which results in considerably higher yields;
(C) reacting compounds of formula (X) with compounds of the formula Y—H in the presence of platinum metals and/or compounds thereof to give compounds of formula (XI)

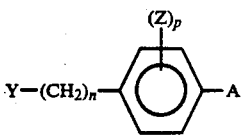 (XI)

in which A, Y, Z, n and p are the same as above.
The compounds of formula (XI) can subsequently be reacted as follows:
(D1) if X in the desired product of formula (II) is to be a radical of the formula —COOH, then compounds of formula (XI), in which A is a radical with the meaning Q, are reacted with magnesium and subsequently with $CO_2$,
(D2) if X in the desired product of formula (II) is to be a radical of the formula —CN, then compounds of formula (XI), in which A is a radical with the meaning Q, are reacted with cyanides, preferably with copper cyanide,
(D3) if X in the desired product of formula (II) is to be a radical of the formula —OH and the radical A in the formula (XI) is a hydroxyl group which is blocked by a protecting group, then the protecting group is removed in a manner known per se, and
(D4) if X in the desired product of formula (II) is to be a radical of the formula —CHO, then compounds of formula (XI), in which A is a radical with the meaning Q, are reacted with magnesium and then with N,N-dimethylformamide and thereafter the product is subjected to acid hydrolysis.

Process 3

The process described above can also be varied, if A in formulas (VII), (VIII) and (X) is a hydroxyl group which is blocked by a protecting group, by removing the protecting group from the compound of formula (X) as early as after step (B).

Process 4

The starting compounds of formula (V) in which m represents 1, i.e., those of formula (XII)

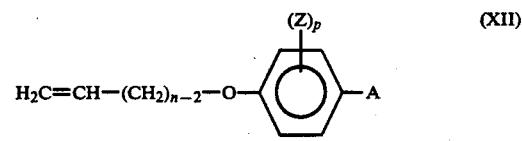 (XII)

are preferably prepared by reacting compounds of formula (XIII)

 (XIII)

with compounds of formula (XIV)

$H_2C=CH-(CH_2)_{n-2}-Q$ (XIV)

where in the above formulas (XIII) and (XIV), A, Q, Z, n and p are the same as above.
In formula (XIV), Q preferably represents a bromine atom. The reaction is carried out in a manner known per se. The corresponding reaction is described, inter alia, in U.S. Pat. No. 4,358,391, to H. Finkelmann et al, Wacker-Chemie GmbH.

Process (5)

Compounds of formula (II) can also be prepared by
(A) reacting compounds of formula (XVI)

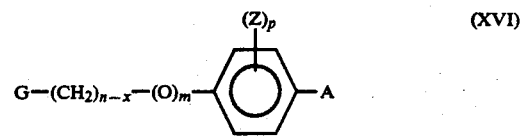 (XVI)

with compounds of the formula (XVII)

$Y-(CH_2)_x-E$ (XVII)

where in the above formulas (XVI) and XVII), one of the radicals E or G is a radical of the formula —Mg—Q and the other radical is in each case a radical with the meaning Q or a hydroxyl radical which is blocked by a protecting group, x represents an integer of from 0 to n−1, with the proviso that if E represents —Mg—Q, and the radical —(CH₂)ₓ—E in the formula (XVII) is bonded directly to a silicon atom, x has a value of at least 1, and A, Y, Z, n, m and p are as defined in formula (II) or in formula (V), and (B) further processing the resultant compound of formula (VI) as in process (1), second step.

All the above mentioned reactions with organomagnesium compounds as reactants can, as is known to those skilled in the art, be carried out with other organometallic compounds, such as for example, with organolithium compounds.

Process (6)

Compounds of formula (II) in which X represents a radical of the formula —NR₂, and m has the value 1, can be prepared by reacting compounds of formula (XVIII)

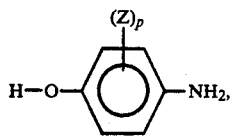          (XVIII)

after blocking the amino group by a protecting group, with compounds of formula (XIX)

Y—(CH₂)ₙ—Σ          (XIX),

Σ is a good leaving group which is known per se, preferably a p-toluenesulfonyl group, and in the above formulas (XVIII) and (XIX), Y, Z, n and p are the same as defined in formula (II), and thereafter the protecting group blocking the amino group is removed.

Protecting groups for the amino group are known in the art. In the present process, it is preferred to block the amino group by forming a Schiff base. This is generally carried out by reaction with an appropriate aldehyde. In the present case, the preferred aldehyde is benzaldehyde. The protecting group can be removed in an acid medium, for example, in methanolic hydrochloric acid.

The compounds described above and similar compounds, namely compounds of formula (XV)

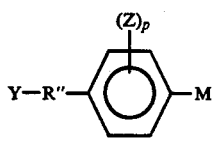          (XV)

in which
M represents a halogen atom, a cyano radical or a radical of the formula —OH, —COOH or —COCl, and Y, Z, R″ and p are the same as above, can be used as starting materials for the preparation of compounds having liquid-crystalline properties.

They can be employed, in particular, as starting compounds for the silylated benzoic acid esters, some of which are liquid-crystalline. (Described in German Patent Application P 39 20 509.6, filed on 22 Jun. 1989, W. Haas et al, Consortium für elektrochemische Industrie GmbH).

Preferred halogen atoms M are chlorine or bromine atoms. If M represents a halogen atom, the compounds of formula (XV) are preferably first reacted in the manner outlined above with magnesium and subsequently with CO₂ to form the corresponding acids. The resultant acids or the compounds of formula (XV) in which M represents a group of the formula —COOH are preferably subsequently reacted, in a manner known per se, to form the corresponding acid halides. The resultant acid halides or the compounds of formula (XV) in which M represents a group of the formula —COCl are reacted with an alcohol to give a molecule containing a mesogenic group. Correspondingly, compounds of formula (XV) in which M represents a group of the formula —CN can be reacted in a manner known per se, after hydrolysis, to form a corresponding acid. By contrast, compounds of formula (XV) in which M represents a hydroxyl group are preferably reacted with appropriately selected acids or acid halides to give the desired molecules containing mesogenic groups.

Compounds of formula (XV) in which M represents a radical of the formula —CHO can be reacted in a manner known per se with amines, for example, 4-substituted anilines, to give Schiff bases. In addition, the same compounds can be reacted with Grignard compounds to give the corresponding hydroxyalkyl compounds. The latter can be reacted through elimination of water to form stilbenes, which in turn can be hydrogenated to give substituted ethylene compounds. In an analogous manner, compounds of formula (XV) in which M represents a radical of the formula —NH₂ can also be reacted with aldehydes, for example with 4-substituted benzaldehydes. Schiff bases and stilbenes are described in large number in the literature cited at the beginning as mesogenic groups or structural features for mesogenic groups.

Mesogenic groups are groups which are able to bring about liquid-crystalline properties in a molecule. Mesogenic groups and corresponding liquid-crystalline compounds are known, inter alia, from D. D. Demus, H. Demus and H. Zaschke [Flüssige Kristalle in Tabellen, (Liquid Crystals in Tables), 1974; D. Demus and H. Zaschke, Flüssige Kristalle in Tabellen II (Liquid Crystals in Tables II), 1984, VEB-Verlag Leipzig]. U.S. Pat. No. 4,358,391 (H. Finkelmann et al, Wacker-Chemie GmbH) describes liquid-crystalline polymers having an organopolysiloxane backbone and mesogenic side groups.

It is preferred that p have a value of 0 in each of the abovementioned formulas (I), (II), (V), (VI), (VII), (VIII), (X), (XI), (XII), (XIII), (XV) and (XVI).

In the following examples, (a) all amounts are based on weight; (b) all pressures are 0.10 MPa (abs.); and (c) all temperatures are 20° C., unless otherwise specified.

EXAMPLE 1

(A) Preparation of compounds of formula (X):

A solution containing 294 g (2 Mol) of 1,4-dichlorobenzene in 500 ml of anhydrous tetrahydrofuran was added dropwise at 80° C. under nitrogen over a period of 110 minutes to a stirred suspension of 48.6 g (2.0 Mol) of magnesium turnings. The mixture was subsequently heated at 80° to 84° C. for an additional 2 hours, then decanted off from the excess magnesium. The resultant solution of Grignard compound was added dropwise at 80° C. over a period of 30 minutes to a stirred solution containing 194 g (1.8 Mol) of 6-bromo-1-hexene (commercially available from Fluka GmbH, D-7910 Neu-Ulm) in 200 ml of tetrahydrofuran. The mixture was then stirred at 80° for an additional four hours and poured onto ice. The mixture was acidified using hydrochloric acid and extracted three times using a 1:1 mixture of diethyl ether/methyl tert-butyl ether, and the ether fractions were stirred with activated charcoal and dried over sodium sulfate. After the filtrate had been evaporated, the residue was fractionated under reduced pressure. About 156 g (corresponding to a yield of 40 percent of theory) of 4-(5-hexenyl)-1-chlorobenzene were obtained at a pressure of 13 hPa and at a temperature of 116° to 118° C. 4-(4-pentenyl)-1-chlorobenzene (b.p. 102° to 105° C. at 13 hPa), 4-(11-dodecenyl)-1-chlorobenzene (b.p. 147° to 150° at 0.2 hPa) and 4-(8-nonenyl)-1-chlorobenzene (b.p. 87° C. at 0.3 hPa) can also be prepared in the same manner.

(B) Preparation of compounds of the formula (XI)

About 15.9 g (0.082 Mol) of 4-(5-hexenyl)-1-chlorobenzene were dissolved in 10 ml of toluene, 0.8 ml of a 1 percent solution of dicyclopentadienylplatinum dichloride in dichloromethane (corresponding to 100 ppm of Pt) were added, and the mixture was introduced into a 100 ml bench autoclave. About 10 g (0.147 Mol) of trimethylsilane in the condensed state were added, the autoclave was sealed, and 5 MPa of nitrogen were injected. The mixture was warmed at 70° to 80° C. for 90 minutes (8 MPa, internal stirring). The mixture was then cooled, the solvent was stripped off, and the resultant residue fractionated. About 17.6 g of 4-(1-trimethylsilylhexyl)-1-chlorobenzene, corresponding to 77.1 percent of theory, were obtained at 0.1 hPa and at a boiling range of 107° to 112° C.

The following derivatives can be obtained in a similar manner:

4-(1-trimethylsilylpropyl)-1-chlorobenzene; b.p. 115° to 118° C. at 15 hPa.
4-(1-dimethylethylsilylbutyl)-1-bromobenzene; b.p. 110° to 112° C. at 0.05 hPa.
4-(1-trimethylsilylpentyl)-1-chlorobenzene; b.p. 148° to 149° C. at 2 hPa.
4-[1-(pentamethyldisiloxanyl)ethyl]-1-bromobenzene; b.p. 128° C. at 0.1 hPa.
4-(1-trimethylsilyldecyl)-1-chlorobenzene; b.p. 127° C. at 0.03 hPa.
4-(4,4-dimethyl-1-trimethylsilyl-4-silaoctyl)-1-chlorobenzene, b.p. 126° to 128° C. at 0.2 hPa.
(=Me$_3$Si—CH$_2$—CH$_2$—CH$_2$—SiMe$_2$—(CH$_2$)$_4$—C$_6$H$_4$—Cl).
4-[1-(butyldimethylsilyl)butyl]-1-chlorobenzene; b.p. 135° C. at 1 hPa.
4-[(1-trimethylsilyl)nonyl]-1-chlorobenzene; b.p. 120° C. at 0.03 hPa.

(C). Preparation of the compounds of formula (I), where X=—COOH.

About 17.6 g (0.063 Mol) of 4-(1-trimethylsilylhexyl)-1-chlorobenzene were dissolved in 17 ml of tetrahydrofuran. About 5 ml of this mixture were added to 2 g (0.082 Mol) of magnesium in a flask, and the mixture was warmed to 60° C. Three drops of ethyl iodide were then added as initiator, and the mixture was refluxed until an internal temperature of 86° C. had been reached. The remainder of the mixture was then added dropwise at a rate such that the internal temperature did not exceed 93° C. Towards the end of the reaction, the temperature was stabilized by the dropwise addition of 8 ml of pure tetrahydrofuran.

After a reaction time of 10 hours, the mixture was cooled and decanted from excess magnesium, and the solution of the Grignard compound was added at 0° to 10° C. to tetrahydrofuran which was saturated with carbon dioxide. After 40 minutes, the mixture was boiled briefly, poured onto ice and acidified. After separation of the phases, the aqueous phase was extracted 4 times with methyl tert-butyl ether, and the ether phases were then collected, dried and evaporated. The residue was recrystallized from heptane to give 12 g of 4-(1-trimethylsilylhexyl)benzoic acid having a melting point of 131.5° C. The 12 g of acid, which were obtained, corresponded to a yield of 68.5 percent of theory.

The following can be obtained in a similar/manner:
4-(1-trimethylsilylpropyl)benzoic acid, m.p. 119° C.
4-(1-trimethylsilylbutyl)benzoic acid, m.p. 178°-179.5° C.
4-(1-dimethylethylsilylpropyl)benzoic acid, m.p. 151°-153° C.
4-[1-(pentamethyldisiloxanyl)ethyl]benzoic acid, m.p. 134°-135° C.
4-(1-trimethylsilylpentyl)benzoic aid, m.p. 105° C.
4-(1-trimethylsilyldecyl)benzoic acid. m.p. 104° C.
4-(1-trimethylsilylhexyl)benzoic acid, m.p. 132° C.
4-(1-trimethylsilylheptyl)benzoic acid, m.p. 99° C.
4-(1-trimethylsilyloctyl)benzoic acid, m p. 116° C.
4-(1-trimethylsilylnonyl)benzoic acid, m.p. 79°-80° C.
4-(1-n-butyldimethylsilylbutyl)benzoic acid, m.p. 91° C.

The following can be prepared in a similar manner using the above procedure by using other silanes or siloxanes in the hydrosilylation:
4-(1-dimethyl-n-hexylsilylpentyl)benzoic acid
4-[1-(pentamethyldisiloxanyl)propyl]benzoic acid
4-[1-(pentamethyldisiloxanyl)butyl]benzoic acid
4-[1-(pentamethyldisiloxanyl)hexyl]benzoic acid
4-[1-(pentamethyldisiloxanyl)octyl]benzoic acid
4-[1-(heptamethyltrisiloxanyl)propyl]benzoic acid
4-[1-(heptamethylcyclotetrasiloxanyl)propyl]benzoic acid
4-[1-(heptamethylcyclotetrasiloxanyl)butyl]benzoic acid

EXAMPLE 2

Preparation of the compounds of formula (I), where X=—OH

4-Methoxymethoxy-1-bromobenzene was prepared from formaldehyde dimethyl acetal and 4-bromophenol by the method of Y. P. Yardley and H. Fletcher, Synthesis 1976, p. 244. The boiling point of this derivative is 54° to 56° C. at 0.1 hPa, and the yield is 49 percent theory.

About 4.6 g (0.19 Mol) of magnesium turnings were moistened with absolute tetrahydrofuran under nitrogen, warmed to 60° C. and treated with a few drops of 4-methoxy-methoxy-1-bromobenzene and a few drops of ethyl iodide as initiator. After the reaction had commenced, the remainder of a total of 35 g (0.16 Mol) of the bromine compound, dissolved in 150 ml of tetrahydrofuran (THF), was added at such a rate that the mixture continued to boil, and the mixture was subsequently refluxed for an additional 2.5 hours. A catalytic amount of a solution of dilithium tetrachlorocuprate (containing 5 percent of dilithium tetrabromocuprate)

and 16.2 ml (0.16 Mol) of 4-bromo-1-butene, dissolved in 200 ml of THF, were then added. The mixture was refluxed for 16 hours, then cooled and poured over ice. The mixture was acidified, the phases were separated, and the aqueous phase was extracted twice with 400 ml of methyl tert-butyl ether. The organic phases were dried and evaporated. The residue was fractionated under reduced pressure. About 16.5 g (corresponding to 53.6 percent of theory) of 4-(methoxymethoxy)-1-(3-butenyl)benzene were obtained having a boiling point of 118° to 120° C. at a pressure of 15 hPa.

By warming this derivative to 95° to 100° C. (40 hours) with 2N acetic acid, 4-(3-butenyl)phenol was liberated. About 20.8 g of 4-(3-butenyl)phenol (42.1 percent of theory) were obtained at a pressure of 16 hPa and at 130° to 140° C.

Instead of the cleavage described, the silylation can also be carried out directly if a protecting group is still present. About 19.2 g (0.1 Mol) of 4-(methoxymethoxy)-1-(3-butenyl)benzene were dissolved in 70 ml of toluene, 13.8 g (0.1 Mol) of pentamethyldisiloxane and 100 ppm of platinum (in the form of a 0.5 percent solution of dicyclopentadieneplatinum dichloride in dichloromethane) were added, and the mixture was heated at 90° C. for 60 minutes. After cooling, the solvent was removed by evaporation, and the residue was cleaved for 40 hours using excess 2N acetic acid. After re-evaporation in vacuo, the residue was subjected to vacuum distillation. About 14.2 g of 4-[(1-pentamethyldisiloxanyl)-butyl]phenol (corresponding to a yield of 73.8 percent of theory) were obtained at a pressure of 0.2 hPa and a boiling range of 113° to 115° C. $^1$H-NMR spectrum (in $CDCl_3$):0.1 ppm (several s, 5 $CH_3$ on both Si atoms), 0.5 to 0.6 ppm (m, $-SiMe_2-CH_2$), 1.3 to 1.5 ppm (m, $-SiMe_2-CH_2$), 1.5 to 1.7 ppm (q, J=6.5 Hz, $C_6H_4-CH_2-C_2$), 2.6 ppm (t, J=6.5 Hz, $C_6H_4-CH_2$), 4.9 ppm (s, $C_6H_4OH$) and 6.7 to 7.1 ppm (m, 4 aromatic H) in the ratio 15:2:2:2:2:1:4.

4-(1-Trimethylsilylbutyl)phenol (b.p. 100° C. at 0.3 hPa) can also be prepared in the same manner.

EXAMPLE 3

(A) About 20.0 g (95 mMol) of 4-(3-butenyl)-1-bromobenzene [which can be prepared, for example, by the method of P. E. Peterson et al, J. Org. Chem. 33, 972 (1968)] were dissolved in 40 ml of toluene, 2 ml of a platinum catalyst solution (0.5 percent solution of cyclopentadiene-platinum dichloride in dichloromethane) were added, and the mixture was added dropwise to a stirred solution containing 16 g (0.18 Mol) of commercially available dimethylethylsilane in 20 ml of toluene. The mixture was stirred at 50° to 70° C. for 3 hours and then cooled, and the solvent was removed by distillation. The residue was fractionated under reduced pressure. Approximately 19.4 g of 4-[4-(dimethylethylsilyl)-butyl]-1-bromobenzene (67.9 percent yield) were obtained at a pressure of 0.05 hPa and at a temperature of 110° to 112° C. A mixture containing 18 g (0.06 Mol) of this derivative, 6.3 g (0.07 Mol) of CuCN and 10 ml of dimethylformamide was heated at 160° C. for 8 hours. The mixture, still hot at 80° C., was poured into a mixture containing 30 g of iron(III) chloride, 7.5 ml of concentrated hydrochloric acid and 90 ml of water, and the full mixture was stirred at 70° C. for 75 minutes. The product was then extracted with tert-butyl methyl ether, the extract was washed, dried and evaporated, and the residue was fractionated. About 9.9 g of 4-[4-(dimethylethylsilyl)butyl]benzonitrile were obtained at 0.02 hPa and at 114° to 116° C. (66.6 percent yield).

(B) About 9.9 g (0.04 Mol) of this nitrile were refluxed for 4.5 hours with 7.5 g of KOH, 20 ml of water and 20 ml of methanol. The mixture was subsequently evaporated, acidified and filtered. After drying, 8.8 g of 4-[4(dimethylethylsilyl)butyl]benzoic acid (83 percent yield) were obtained. The melting point of the acid is 151° to 153° C.

EXAMPLE 4

(A) About 12.3 g (0.1 Mol) of commercially available chloromethyltrimethylsilane were dissolved in 100 ml of diethyl ether, and 2 ml of this solution were added under an inert gas to a mixture containing 3 g of magnesium turnings and one drop of ethyl iodide. After the reaction had been initiated by warming, the remainder of the silane/ether mixture was added dropwise at 20° C. with stirring over a period of one hour. When the addition was complete, the mixture was refluxed for an additional 30 minutes, then cooled and decanted from the excess magnesium. The resultant solution was added dropwise over a period of 30 minutes with stirring at 20° to 30° C. to a solution containing 22.7 g (0.1 Mol) of 2-(4-chlorophenyl)ethyl toluene sulfonate (obtained from commercially available 2-(4-chlorophenyl)ethanol by the known reaction with toluene sulfonyl chloride) in 100 ml of tetrahydrofuran. When the addition was complete, 100 ml of the solvent mixture were removed by distillation and replaced by 50 ml of tetrahydrofuran. The mixture was heated at an internal temperature of 60° C. for 60 minutes, during which time magnesium tosylate precipitated. After cooling, the mixture was poured over ice and acidified with a little hydrochloric acid, and the aqueous phase was extracted twice with tert-butyl methyl ether. The collected organic phases were washed with NaCl solution, dried and evaporated. About 17.1 g (75.4 percent yield) of 1-chloro-4-(1-trimethylsilylpropyl)benzene were obtained by fractional distillation of the residue at 16 hPa and at 115° to 118° C.

(B) About 7 ml of a 1:1 mixture of the silane which can be prepared as in (A) and tetrahydrofuran to initiate the reaction were added at 40° C. to 2 g of magnesium in a flask. When an internal temperature of 75° C. had been reached, the remainder of the silane/THF mixture (corresponding to 14 g of the silane) was added dropwise over a period of 30 minutes without external heating. The mixture was subsequently refluxed for 1 hour and then cooled, and the excess magnesium was filtered off.

This Grignard solution was added at 0° to 10° C. to tetrahydrofuran which was saturated with carbon dioxide. Carbon dioxide was passed through the mixture for an additional 40 minutes, and the mixture was then briefly boiled and poured over ice. The mixture was acidified, the phases were separated, the aqueous phase was extracted with tert-butyl methyl ether, and the organic phases were washed, dried and evaporated. The residue was recrystallized from heptane to give 11.4 g of 4-(1-trimethylsilylbutyl)benzoic acid (64.6 percent yield) with a melting point of from 178° to 179.5° C.

EXAMPLE 5

In the same manner as described in Example 1, a Grignard solution in a mixture containing 450 ml of toluene and 40 ml of tetrahydrofuran was prepared from 58.8 g (0.4 Mol) of 1,4-dichlorobenzene. A solution of 146.4 g (0.6 Mol) of commercially available 1,6-dibromobenzene in 100 ml of toluene and a catalytic amount of dilithium tetrachlorocuprate were added to this solution. The full mixture was refluxed for 7 hours. The precipitate was then filtered off, the filtrate was acidified, and the phases were separated. The organic phase was washed, dried and evaporated, and the residue was fractionated. About 50 g of 1-(6-bromohexyl)-4-chlorobenzene (45 percent yield) were obtained at a pressure of 0.2 hPa and at 106° to 109° C.

Approximately 2 g (82 mMol) of magnesium in a flask were moistened with tetrahydrofuran. A Grignard reaction was initiated using 5 drops of 1-(6-bromohexyl)-4-chlorobenzene. The remainder of a total of 17 g of the halogen compound (61 mMol), dissolved in 50 ml of tetrahydrofuran, was added dropwise at 50° to 60° C. When the addition was complete, the mixture was kept at this temperature for an additional 2.5 hours, and a solution of 12 g (110 mMol) of trimethylchlorosilane and a catalytic amount of dilithium tetrachlorocuprate in 40 ml of tetrahydrofuran was then added dropwise at 20° to 40° C. The mixture was stirred at 60° C. for 1 hour, then allowed to stand overnight and diluted with 200 ml of tert-butyl methyl ether. The mixture was then acidified using 2N sulfuric acid, the phases were separated, and the organic phase was washed and dried. The evaporated residue was fractionated. About 6.4 g of 1-chloro-4-(1-trimethylsilylhexyl)benzene (38.6 percent yield) were obtained at a pressure of 0.2 hPa and at 88° to 90° C.

EXAMPLE 6

4-(3-Butenyl)benzoic acid was prepared as in Example 3 and reacted with excess chlorotrimethylsilane to form trimethylsilyl 4-(3-butenyl)benzoate (b.p. 100° to 102° C. at 0.1 hPa). About 20.0 g (80.5 mMol) of this ester were dissolved in 60 ml of toluene, 1 ml of a 0.5 percent solution of cyclopentadienylplatinum dichloride in dichloromethane and 22.8 g (80.5 mMol) of 1,3,3,5,5,7,7-heptamethylcyclotetrasiloxane were added, and the mixture was kept at 60° to 80° C. for 4 hours. The ester was then hydrolyzed using excess methanol/water, the methanol was stripped off, and the acid was precipitated from the water which remained. The precipitate was dissolved in petroleum ether, the solution was boiled with activated charcoal and filtered, and the product was re-precipitated to give 26.5 g of 4-[1(heptamethylcyclotetrasiloxanyl)butyl]-benzoic acid (75.3 percent yield) having a melting point of 72° to 78° C.

EXAMPLE 7

About 6.21 g (23.5 mMol) of 4-(5-hexenyloxy)-1-trimethylsilyloxy benzene, 3.48 g (23.5 mMol) of pentamethyldisiloxane and 694 mg (17.7 μMol of Pt) of 0.5 percent cyclopentadienylplatinum dichloride solution (dichloromethane) were refluxed for 7 hours in 25 ml of toluene. After the hydrosilylation was complete, the toluene was removed by vacuum distillation on a rotary evaporator. The crude product was purified by chromatography on silica gel. Further chromatography on silica gel using petroleum ether/ethyl acetate mixtures on a Harrison Research chromatotron gave 94 percent pure 4-(1-pentamethyldisiloxanylhexyloxy)phenol as a pale yellow liquid.

The following was prepared analogously: 4-(1-trimethylsilylhexyloxy)phenol, 99 percent pure, pale yellow liquid.

EXAMPLE 8

A Grignard compound was prepared as in Example 1(C) from 3.5 g (0.24 Mol) of magnesium and 31.6 g (0.13 Mol) of 4-(1-trimethylsilylbutyl)-1-chlorobenzene, and decanted off from the excess magnesium. The solution was added dropwise at 5° to 10° C. with stirring to a solution containing 13.2 ml of dimethylformamide in 200 ml of tetrahydrofuran over a period of 30 minutes, and the mixture was stirred for an additional hour. The mixture was subsequently poured over ice and acidified using hydrochloric acid. The organic components were extracted with methyl tert-butyl ether, and the extract was washed, dried and evaporated. The residue was fractionated to give 19.1 g (62.1 percent of theory) of 4-(1-trimethylsilylbutyl)benzaldehyde at 102° to 103° C. and 0.04 hPa.

EXAMPLE 9

About 26.5 g (0.25 Mol) of benzaldehyde were added dropwise at 40° to 60° C. with stirring to a mixture containing 27.3 g (0.25 Mol) of 4-aminophenol, 21.5 ml of hydrochloric acid (36 percent strength) and 300 ml of water. The resultant yellow suspension was adjusted to pH 5 to 6 using NaOH, and this mixture was heated at 95° C. for 30 minutes. The mixture was then cooled, and the crystals were filtered off, dried and recrystallized from methanol.

Approximately 19.7 g (0.1 Mol) of this derivative were dissolved in methanol, a solution containing 5.4 g of sodium methylate in methanol was added dropwise with stirring, and a solution containing 29.7 g (0.1 Mol) of 6-trimethylsilylhex-1-yl toluenesulfonate was added dropwise at 20° C. The mixture was refluxed for 3 days and then cooled, and the resultant sodium tosylate was removed. After the methanol had been stripped off, the residue was added to acetonitrile, again refluxed for 2 hours and again cooled, and the remainder of the sodium tosylate was separated off. The solvent was removed by distillation, and the residue was shaken with water/tert-butyl methyl ether. Phase separation, washing, drying and evaporation gave 24.4 g (68.8 percent of theory) of N-benzylidene-4-(1-trimethylsilylhexyloxy)aniline.

The resultant derivative was cleaved using hydrochloric acid in methanol; the organic phases were separated off; and 4-(1-trimethylsilylhexyloxy)aniline was liberated by extracting the basified residue by shaking.

1-Trimethylsilylhexyl toluenesulfonate was obtained as follows: Commercially available 5-hexen-1-ol was converted into 5-hexenyl trimethylsilyl ether (boiling point 78° C. at a pressure of 32 hPa) using trimethylsilyl chloride/triethylamine in toluene as solvent. This compound was silylated at the double bond as described in Example 7 using a molar amount of commercially available trimethylsilane and a catalytic amount of dicyclopentadienylplatinum dichloride in a bench autoclave. The boiling point of the resultant 1-trimethylsilylhexyl trimethylsilyl ether at a pressure of 2 hPa was 73° to 74° C. 1-Trimethylsilylhexanol was liberated by removing the trimethylsilyl protecting group using ethanol/NaOH and was converted into the desired ester in a customary manner using tosyl chloride.

EXAMPLE 10

Preparation of dinuclear phenol

About 50 g (0.2 Mol) of commercially available 4-bromo-4'-hydroxybiphenyl (TCI Chemicals/G. Karl GmbH, 6222 Geisenheim) were reacted in a known manner with 2H-3,4-dihydropyran to give 4'-bromobiphenylyl tetrahydropyranyl ether. About 33.3 g (0.1 Mol) of this compound were dissolved in 170 ml of dry tetrahydrofuran, 5 ml of this solution were added to 29.2 g (0.12 Mol) of magnesium turnings, and a Grignard reaction was initiated by adding a little iodine. The remainder of the solution was then added dropwise at 50° to 60° C. with stirring, and the mixture was refluxed for 3 hours, cooled and decanted.

A catalytic amount of $Li_2CuCl_4/Li_2CuBr_4$ (1:1) was added to a solution containing 32.8 g (0.1 Mol) of 6-trimethylsilylhex-1-yl toluene sulfonate (preparation is described in Example 9) in 150 ml of tetrahydrofuran, and the solution of the Grignard compound described above was added dropwise with stirring. The mixture was refluxed for 6 hours and then cooled, and the precipitate was separated off. Hydrolysis, purification and drying gave 4-hydroxy-4'-(6-trimethylsilylhex-1-yl)biphenyl.

$^1$H-NMR (in $CDCl_3$): 0.0 ppm (s, $Me_3Si$), 0.5 ppm (t, $Me_3Si—CH_2$), 1.3 ppm (m, $3CH_2$), 1.6 ppm (t, $—C_6H_4—CH_2—CH_2—$), 3.7 ppm (t, $—C_6H_4—CH_2$), 5.6 ppm (s, $HO—C_6H_4—$), 6.8 to 7.5 ppm (m, series of doublets, 8 aromatic H).

What is claimed is:

1. A compound capable of being converted to a liquid crystal having the formula

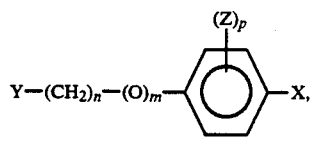

(II)

in which n is an integer having a value of at least 2; m is an integer having a value of 1, where the sum of n+m is at least 3; X is a radical selected from the group consisting of the formula —COOH, —CN, —CHO, and —OH, in which the hydroxyl group may be blocked by a protecting group; Y is an organosilicon radical; Z is a substituent in the 2-, 3-, 5- or 6-position to the radical X, and p has a value of from 0 to 4.

2. The compound of claim 1, where in the formula (II), Y is a radical selected from the group consisting of a linear silanyl and siloxanyl radical selected from the group consisting of formula (III)

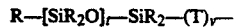

(III)

and a cyclosiloxanyl radical of formula (IV)

(IV),

R is the same or different radical selected from the group consisting of a hydrocarbon radical having from 1 to 18 carbon atoms and a substituted hydrocarbon radical having from 1 to 18 carbon atoms, whose substituents are selected from the group consisting of halogen atoms, cyano radicals, mercapto groups and amino groups; t is an integer having a value of at least 0; u is an integer having a value of at least 2, and a maximum of 8; v is an integer having a value of at least 0, and a maximum of 5; T is a radical of the formula $—R''''—SiR_2—$, where R is the same as above; and R'''' is selected from the group consisting of a divalent hydrocarbon radical having up to 20 carbon atoms and a substituted divalent hydrocarbon radical having up to 20 carbon atoms.

3. A process for preparing the compound of claim 2, which comprises reacting a compound of formula (V)

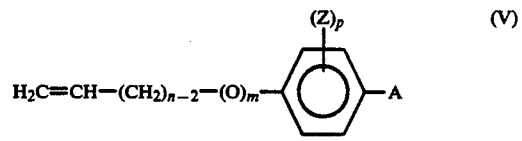

(V)

in which

A is selected from the group consisting of Q, a hydroxyl group and a carboxyl group which is blocked by a protecting group;

Q is a halogen atom;

with a compound of the formula Y—H in the presence of a catalyst selected from the group consisting of platinum metals and compounds thereof to form a compound of the formula (VI),

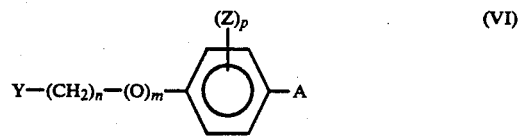

(VI)

where

Z is a substituent in the 2-, 3-, 5-, or 6- position to the radical A;

Y is an organosilicon radical;

m is an integer having a value of 1;

n is an integer having a value of at least 2;

p has a value of 0 or from 0 to 4;

and when X in formula (II) is a radical of the formula —COOH, then reacting the compound of formula (VI), in which A is radical Q, with magnesium and thereafter with $CO_2$.

4. The process of claim 3, in which in the compound of formula (VI), A is a carboxyl radical blocked by a protecting group and thereafter the protecting group is moved.

5. The process of claim 3, in which the compound of formula (VI), in which A is a radical Q, is reacted with a cyanide.

6. The process of claim 3, in which A in the compound of formula (VI), is a hydroxyl group blocked by a protecting group, and thereafter the protecting group is removed.

7. The process of claim 3, wherein the compound of formula (VI), in which A is the radical Q, is reacted with magnesium, and then with N,N-dimethylformamide and thereafter the resultant product is subjected to acid hydrolysis.

8. The process of claim 3, in which the compound of formula (V) employed in step (A)

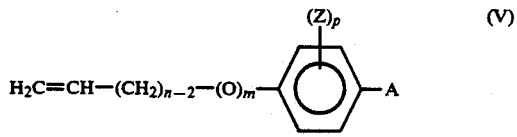

(V)

is prepared by reacting a compound of the formula (XIII)

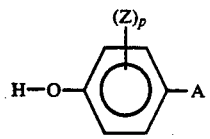

with a compound of the formula (XIV)

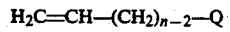

where Z is a substituent in the 2-, 3-, 5- or 6-position to the radical A;
A is selected from the group consisting of Q, a hydroxyl group and a carboxyl group which is blocked by a protecting group;
Q is a halogen atom;
m is an integer having a value of 1;
n is an integer having a value of at least 2 and
p has a value of from 0 to 4.

9. The process of claim 3, wherein p has a value of 0 in formulas (V) and (VI).

10. A process for the preparation of a compound of the formula

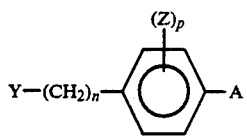

in which
A is selected from the group consisting of Q, and a hydroxyl group which is blocked by a protecting group;
Q is a halogen atom;
Z is a substituent in the 2-, 3-, 5- or 6-position to the radical A;
Y is an organosilicon compound;
n is an integer having a value of at least 2 and
p has a value of from 0 to 4;
which comprises (A) reacting a compound of the formula (VII)

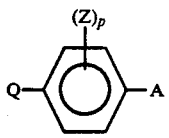

in which A, Q, Z and p are the same as above, with magnesium to give a Grignard compound of the formula (VIII)

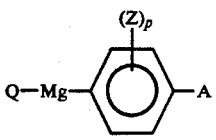

(B) reacting the Grignard compound of formula (VIII) with a compound of formula (IX)

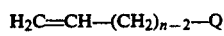

to form a compound of formula (X)

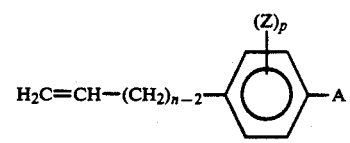

(C) reacting a compound of formula (X) with a compound of the formula Y—H in the presence of a catalyst selected from the group consisting of platinum metals and compounds thereof to form a compound of the formula (XI)

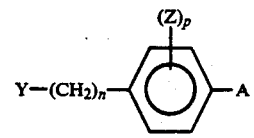

in which A, Q, Z, Y, n and p are the same as above, and when A in formula (XI) is Q, the compound of formula (XI) is reacted with magnesium and thereafter with $CO_2$ to convert radical A to a radical the formula —COOH.

11. The process of claim 10, in which the compound of formula (XI), in which A is a radical Q, is reacted with a cyanide.

12. The process of claim 10, in which the radical A in formula (XI), is a hydroxyl group which is blocked by a protecting group and thereafter the protecting group is removed.

13. The process of claim 10, wherein the compound of formula (XI), in which A is a radical Q, is reacted with magnesium, then with N,N-dimethylformamide and then subsequently the resultant product is subjected to acid hydrolysis.

14. The process of claim 10, in which A in the formulas (VII), (VIII) and (X) is a hydroxyl group blocked by a protecting group, wherein the protecting group is removed from the compound of formula (X) prior to reacting the compound of formula (X) with a compound of the formula Y—H in step (C), in which Y is an organosilicon compound.

15. The process of claim 10, in which A is a carboxyl radical blocked by a protecting group and thereafter the protecting group is removed.

16. The process of claim 10, in which A is a radical Q, and thereafter the resultant compound is reacted with a cyanide.

17. The process of claim 10, in which A is a hydroxyl group which is blocked by a protecting group and thereafter the protecting group is removed.

18. The process of claim 10, in which A is the radical Q, and thereafter the resultant compound is reacted with magnesium, then with N,N-dimethylformamide and thereafter the resultant product is subjected to acid hydrolysis.

19. The process of claim 10, wherein p has a value of 0 in formulas (VII), (VIII), (IX), (X) and (XI).

20. The process of claim 8, wherein p has a value of 0 in formulas (XII) and (XIII).

21. The compound of claim 1, wherein p has a value of 0 in formula (II).

22. A process for preparing a compound of the formula

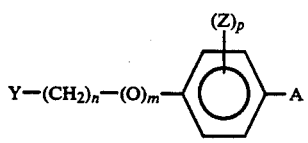  (VI)

which comprises:

(A) reacting a compound of the formula (XVI)

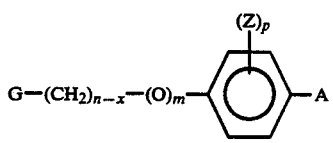  (XVI)

with a compound of formula (XVII)

Y—(CH$_2$)$_x$—E     (XVII)

in which one of the radicals E or G is a radical of the formula —Mg—Q and the other radical is in each case a radical selected from the group consisting of Q and a hydroxyl radical which is blocked by a protecting group; x is an integer of from 0 to n−1, with the proviso that if E represents —Mg—Q and the radical —(CH$_2$)$_x$—E in the formula (XVII) is bonded directly to a silicon atom, x has a value of at least 1;

A is selected from the group consisting of Q, a hydroxyl group and a carboxyl group which is blocked by a protecting group;

Y is an organosilicon compound;

Z is a substituent in the 2-, 3-, 5-, or 6-position to the radical A;

m is an integer having a value of 0 or 1;

n is an integer having a value of at least 2, where the sum of n+m is at least 3;

p has a value of from 0 to 4; and (B) when A in the compound of formula (VI) is a radical Q, then the resultant compound is reacted with magnesium and thereafter with CO$_2$ to convert radical A to a radical of the formula —COOH.

23. The process of claim 16, wherein p has a value of 0 in formula (XVI).

24. A compound of the formula

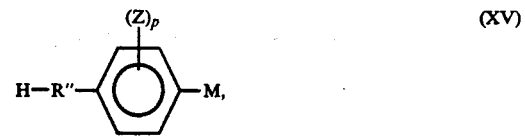  (XV)

in which

M is selected from the group consisting of a halogen atom, a cyano radical, —COCl, —COOH, —CHO, —NH$_2$ and —OH, where the —OH group may be blocked with a protecting group;

Y is an organosilicon radical;

Z is a substituent in the 2-, 3-, 5-, or 6-position to the radical M;

R″ is a divalent radical which connects the radical Y to the benzene ring via a chain of at least three atoms;

p has a value of from 0 to 4.

25. A compound of the formula

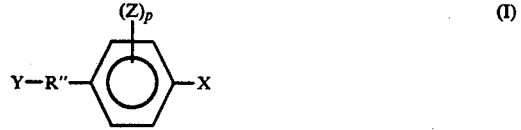  (I)

in which Y is an organosilicon radical, R″ is a radical of the formula —(O)$_q$—R″″$_r$(—O)$_s$—, where R″″ is a divalent hydrocarbon radical having up to 20 carbon atoms or a substituted divalent hydrocarbon radical having up to 20 carbon atoms, q and s each represent a number of 0 or 1, r has a value of 1 to 3 and q, r, s and R″″ are selected so that R″ is a divalent radical which connects Y to the benzene ring via a chain of at least three atoms; X is a radical selected from the group consisting of the formula —COOH, —CN, —CHO and —OH, in which the hydroxyl group may be blocked by a protecting group; Z is a substituent in the 2-, 3-, 5- or 6-position to the radical X; and p has a value of from 0 to 4.

* * * * *